United States Patent [19]

Zaiger et al.

[11] Patent Number: Plant 8,441

[45] Date of Patent: Nov. 2, 1993

[54] NECTARINE TREE 'FLAME GLO'

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of, Modesto, Calif. 95358

[21] Appl. No.: 5,486

[22] Filed: Jan. 15, 1993

[51] Int. Cl.[5] ..... A01H 5/00

[52] U.S. Cl. ..... Plt./41.1

[58] Field of Search ..... Plt. 41.1

[56] References Cited

PUBLICATIONS

Brooks, R. M., et al., "Fireglobe" *Nectarine; Register of New Fruit and Nut Varieties* (2nd Ed.), 1972, University of California Press, Berkeley, p. 299.

*Primary Examiner*—James R. Feyrer

[57] ABSTRACT

Our new development relates to a distinct variety of nectarine tree which has the following unique combination of features that are desirable in a new variety.

1. Heavy and regular production of fruit.
2. Fruit with a high degree of attractive red skin color.
3. Fruit with good flavor and eating quality.
4. Fruit having good storage and shipping quality.
5. Vigorous upright growth.
6. Relatively uniform ripening of fruit throughout the tree.

1 Drawing Sheet

ORIGIN OF THE VARIETY

The present new variety of nectarine tree was originated by us in our experimental orchard located near Modesto, Calif. as a third generation selection from a cross between Flamekist Nectarine (non-patented) and a selected seedling with the field identification number 60G356. The pollen parent with the field identification number 60G356 originated as a selected seedling from a second generation cross between Sun Grand Nectarine (U.S. Plant Pat. No. 974) and merril Gem Peach (U.S. Plant Pat. No. 868). We grew and maintained a large group of these third generation seedlings under careful observation, during which time we recognized the desirable fruit characteristics of the present variety and selected it for asexual reproduction and commercialization.

ASEXUAL REPRODUCTION OF THE VARIETY

Axesual reproduction of the new and distinct variety was performed by budding in our experimental orchard located near Modesto, Calif. and shows that such reproductions run true to the original tree and are established and transmitted through succeeding propagations.

SUMMARY OF THE VARIETY

A new and distinct variety of nectarine tree which is of large size, vigorous, upright growth and a productive and regular bearer of large, yellow flesh, clingstone fruit with good flavor and eating quality. The fruit is further characterized by having a high degree of attractive red skin color, firm flesh with good handling and shipping quality, relative uniform size and maturity throughout the tree and in comparison to Flamekist Nectarine (non-patented) the new variety has firmer flesh, a greater degree of attractive red skin color and matures earlier by approximately 45 days.

DESCRIPTION OF THE PHOTOGRAPHS

The accompanying photographic reproductions in color are of typical specimens of the foliage and fruit of the new variety of nectarine tree.

The upper and lower surface of the leaves being shown with an exterior and sectional view of the fruit being divided in the suture plane to show flesh coloration, pit cavity and a stone remaining in place.

The photographic illustrations were taken shortly after being picked at maturity (shipping ripe) and the colors are as nearly true as is reasonably possible in a color representation of this type.

DESCRIPTION OF THE VARIETY

The following is a detailed botanical description of the new and distinct variety of nectarine tree, its flowers, foliage and fruit, based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Density.*—Medium dense.
- *Form.*—Upright.
- *Production.*—Productive.
- *Bearer.*—Regular.

Trunk:
- *Size.*—Large.
- *Texture.*—Medium shaggy.
- *Color.*—Grayish brown to brown (5-D-4) to (5-D-5).

Branches:
- *Size.*—Medium.
- *Texture.*—Smooth to medium rough.
- *Color.*—Light brown to brown — color varies with maturity.
- *Lenticels.*—Numerous. Large size.

Leaves:
- *Size.*—Large. Average length — 7". Average width — 1½".
- *Form.*—Varies from lanceolate to oblanceolate — pointed.
- *Margin.*—Crenate.

*Thickness.*—Medium.
*Petiole.*—Medium length. Medium thickness.
*Surface.*—Smooth.
*Glands.*—Reniform. Medium size. Number varies from 1 to 4. Average number 2. Located on upper portion of petiole and on base of leaf blade.
*Color.*—Upper surface — green to dark green (27-F-6) to (27-F-8). Lower surface — nickel green to green (27-F-3) to (27-F-5).

Flower buds:
*Size.*—Medium to large.
*Length.*—Medium.
*Form.*—Plump.

Flowers:
*Size.*—Large — showy.
*Blooming period.*—Mar. 3, 1992, to Mar. 10, 1992. Varies slightly with climatic conditions.
*Pollen.*—Present.
*Color.*—Pink.

Fruit:
*Maturity when described.*—Firm ripe.
*Date of first picking.*—Jun. 25, 1992.
Date of last picking.—Jun. 29, 1992.
Size.—Large. Average diameter axially — 2⅞" to 3¼". Average transversely in suture plane — 2¾" to 3".
*Form.*—Nearly Globose, majority of fruit slightly enlarged near suture. Slightly flattened at stem end.
*Suture.*—Shallow — extends from base to apex.
*Ventral surface.*—Nearly round to slightly extending outward on one side of suture.
*Apex.*—Varies from round to very slight pistil point.
*Base.*—Retuse.
*Cavity.*—Rounded to elongated in suture plane. Average depth — ½". Average breadth — ⅞".

Flesh:
*Ripens.*—Evenly.
*Texture.*—Firm.
*Fibers.*—Moderate number — small, tender.
*Juice.*—Moderate.
*Amygdalin.*—Undetected.
*Aroma.*—Moderate.
*Eating quality.*—Good.
*Flavor.*—Good — a good balance between sugar and acid.

*Color.*—Pale yellow to light yellow (4-A-3) to (4-A-5).

Skin:
*Texture.*—Medium tough — tenacious to the flesh.
*Thickness.*—Medium.
*Down.*—Wanting.
*Tendency to crack.*—None.
*Color.*—Light yellow ground color (3-A-4) to (3-A-5). Overspread with red to deep red (11-B-8) to (11-C-8).

Stone:
*Type.*—Clingstone.
*Size.*—Large. Average length — 1½". Average breadth — 1 1/16". Average thickness — ⅝".
*Form.*—Ovate to obovate.
*Apex.*—Usually rounded — varies from rounded to acuminate.
*Side.*—Equal to unequal — surface edges varies from smooth to nearly crenate.
*Base.*—Usually rounded — varies from rounded to straight.
*Surface.*—Irregularly furrowed toward apex, pitted toward base. Ridges vary from rough to rounded and pit cavities vary from elongated to round.
*Tendency to split.*—Very slight.
*Color.*—Brown to reddish brown (8-E-8) to (9-D-8).

Use: Dessert.
*Market.*—Local and long distance.
Keeping quality: Good.
Shipping quality: Good.

The new nectarine tree, its flowers, foliage and fruit herein described may vary in slight detail due to cultural practices, climatic and soil conditions under which the variety may be grown; the present description is that of the variety grown under the ecological conditions prevailing near Modesto, Calif.

We claim:

1. A new and distinct variety of nectarine tree, substantially as illustrated and described, characterized by its large size, vigorous upright growth and a productive and regular bearer of large, firm, yellow flesh, clingstone fruit with good eating, storage and shipping quality; the fruit is further characterized in comparison to Flamekist Nectarine (non-patented) as having firmer flesh, a higher degree of attractive red skin color and maturing earlier by approximately 45 days.

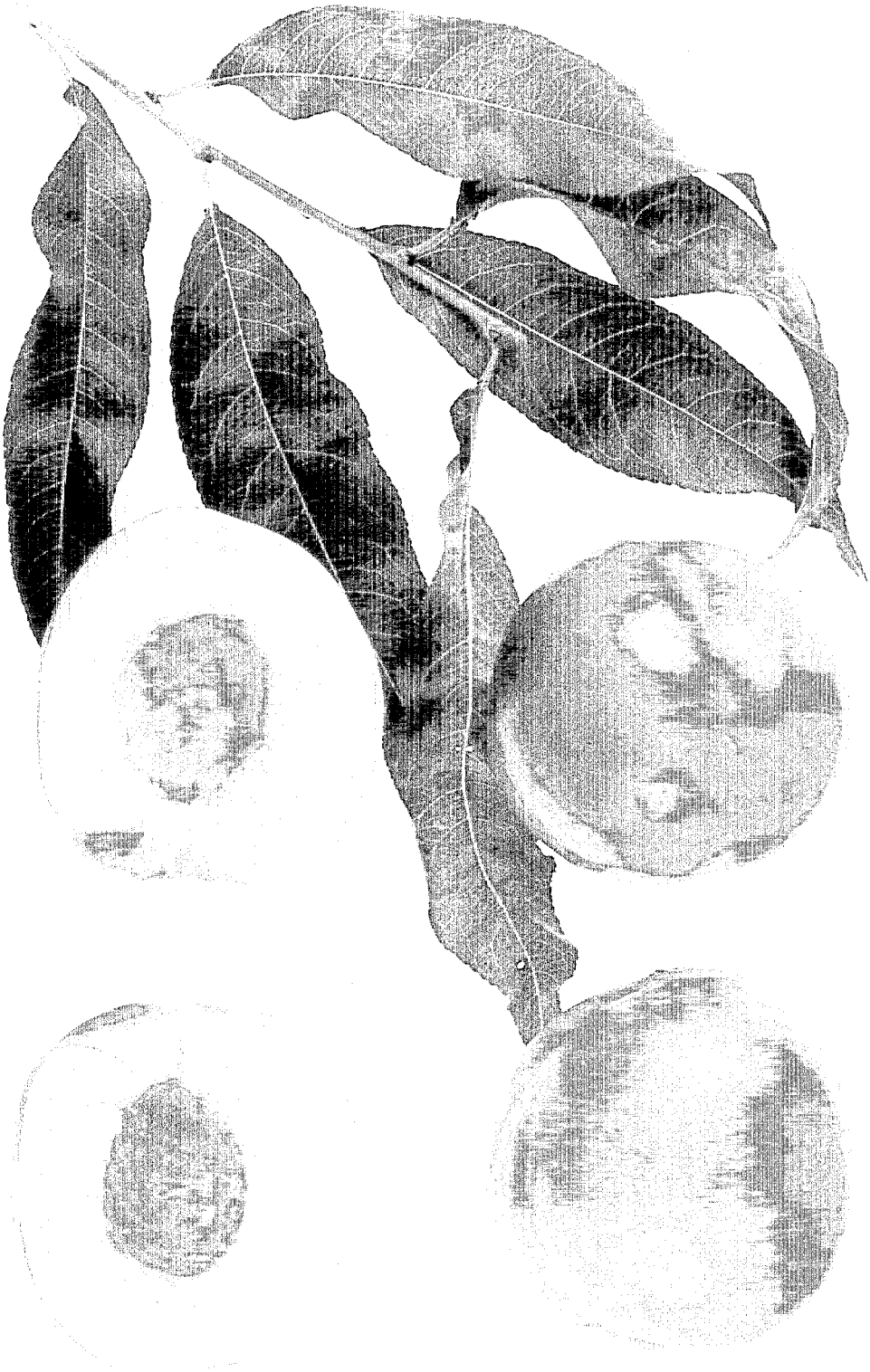

* * * * *